United States Patent
Dandliker et al.

(12)

(10) Patent No.: US 7,371,524 B2
(45) Date of Patent: May 13, 2008

(54) SUBSTITUTED AZAPORPHYRINS AS FLUORESCENCE LABELS

(75) Inventors: Walter B. Dandliker, La Jolla, CA (US); Mao Lin Hsu, Fountain Valley, CA (US); William P. Murphy, Jr., Coral Gables, CA (US)

(73) Assignee: Hannjorg Hereth, Baar (CH)

( * ) Notice: Subject to any disclaimer, the term of this patent is extended or adjusted under 35 U.S.C. 154(b) by 443 days.

(21) Appl. No.: 10/866,361

(22) Filed: Jun. 14, 2004

(65) Prior Publication Data
US 2005/0277119 A1 Dec. 15, 2005

Related U.S. Application Data

(60) Provisional application No. 60/479,249, filed on Jun. 17, 2003.

(51) Int. Cl.
| | |
|---|---|
| *C12Q 1/70* | (2006.01) |
| *C12Q 1/68* | (2006.01) |
| *G01N 33/53* | (2006.01) |
| *G01N 33/533* | (2006.01) |
| *G01N 31/00* | (2006.01) |
| *C07H 19/04* | (2006.01) |
| *A01N 61/00* | (2006.01) |
| *A01N 43/04* | (2006.01) |

(52) U.S. Cl. ............................. 435/6; 435/5; 435/7.1; 435/7.2; 435/968; 536/26.6; 436/2; 436/546; 514/1; 514/44

(58) Field of Classification Search ................. 435/5, 435/6, 7.1, 7.2, 968; 536/26.6; 436/2, 546; 514/1, 44
See application file for complete search history.

(56) References Cited

U.S. PATENT DOCUMENTS

| | | | |
|---|---|---|---|
| 5,135,717 | A | 8/1992 | Renzoni et al. |
| 5,323,008 | A | 6/1994 | Studholme et al. |
| 5,346,670 | A | 9/1994 | Renzoni et al. |
| 5,403,928 | A | 4/1995 | Arrhenuis |
| 5,494,793 | A | 2/1996 | Schindele et al. |
| 5,606,045 | A | 2/1997 | Dandliker et al. |
| 5,641,878 | A | 6/1997 | Dandliker et al. |
| 5,677,199 | A | 10/1997 | Arrhenuis |
| 5,707,813 | A | 1/1998 | Dandliker et al. |
| 5,846,703 | A | 12/1998 | Devlin et al. |
| 5,880,287 | A | 3/1999 | Dandliker et al. |
| 5,919,922 | A | 7/1999 | Dandliker et al. |
| 6,060,598 | A | 5/2000 | Devlin et al. |
| 6,552,199 | B1 | 4/2003 | Daltrozzo |

*Primary Examiner*—Jezia Riley
(74) *Attorney, Agent, or Firm*—Jacobson Holman PLLC

(57) ABSTRACT

The present invention relates to marker components, fluorescent probes, oligonucleotides, hybridization assays, and immunoassays using such products, and methods for making such products. According to the present invention, detectably labeled marker components are provided that comprise a fluorescent moiety coupled to two small solubilizing groups, one on each side of the molecular plane, said fluorescent moiety having substituents to control net charge so as to reduce or remove the problems of solvent sensitivity and nonspecific binding.

7 Claims, 1 Drawing Sheet

Dihydroxysilicondicarboxyphthalocyanine monosulfonate, La Jolla Blue-3.

LJB-3

Synthesis: By the diiminoisoindoline method utilizing a 4:1 ratio of diiminoisoindoline to tetradiiminopyromellitic acid diimide followed by sulfonation by chlorosulfronic acid for 36 hr. at 70 C. Note that the exact position of the sulfonate group is uncertain.

Figure 1. Dihydroxysilicondicarboxyphthalocyanine monosulfonate, La Jolla Blue-3.
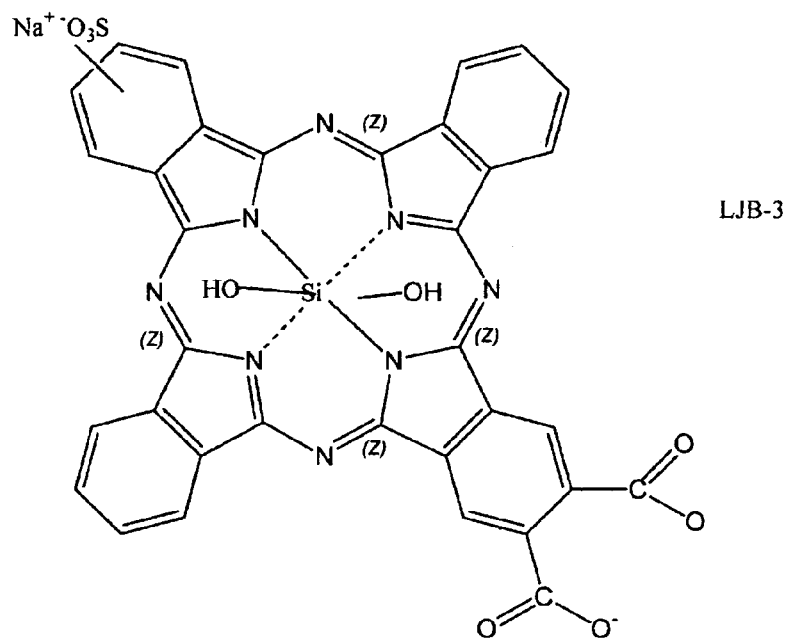
LJB-3
Synthesis: By the diiminoisoindoline method utilizing a 4:1 ratio of diiminoisoindoline to tetradiiminopyromellitic acid diimide followed by sulfonation by chlorosulfronic acid for 36 hr. at 70 C. Note that the exact position of the sulfonate group is uncertain.

US 7,371,524 B2

SUBSTITUTED AZAPORPHYRINS AS FLUORESCENCE LABELS

This patent application claims priority to U.S. Provisional Patent Application Ser. No. 60/479,249, filed Jun. 17, 2003, and is incorporated by reference as if fully set forth herein.

FIELD OF THE INVENTION

This application relates generally to fluorography, fluorometric measurements and fluorescence probes.

BACKGROUND OF THE INVENTION

Publications and other reference materials referred to herein are incorporated herein by this reference. The following description of the background of the invention is intended to aid in the understanding of the invention, but is not admitted to describe or constitute prior art to the invention.

The near infrared absorption and emission of prophyrins, phthalocyanines and other azaporphyrins and certain other aromatic nitrogen containing macrecycles have for some time made these compounds attractive candidates for use as fluorescence labels.

The phthalocyanines, particularly because of their strong near infrared absorption (molar extinction coefficients about 200,000) their high quantum yields and the resistance to fading of common metallophthalocyanine dyes have given rise to many efforts to utilize them as fluorescent labels. However, earlier efforts along these lines did not yield entirely satisfactory products largely because of the unusually strong tendency of phthalocyanines to associate, particularly by stacking in face to face aggregates, and also to bind strongly to a variety of other molecular surfaces (nonspecific binding).

As a result of intramolecular stacking unsubstituted phthalocyanines have very low solubilities in both organic and aqueous solvents. As is now well known, the tendency to stack can be reduced by the introduction of charged groups, such as sulfonate. While phthalocyanines with such substituents may possess high solubility in water and in aqueous solutions of electrolytes, the tendency to bind nonspecifically largely persists. Much of the scientific interest in fluorescence labeling is focused on applications involving biological materials such as tissue sections, cells, cell fragments, proteins, including glycol- and lipo-proteins, peptides, oligo- and poly-saccharides, oligo- and polynucleotides and lipids. A tendency to bind nonspecifically in fluorescence assays involving these materials may interfere by partially masking the specific interactions of interest. The nonspecific binding as well as the tendency to stack can be reduced to levels negligible in assays for therapeutic drugs by coupling the phthalocyanine dye to one or more polyoxyhydrocarbyl groups, typically methoxy-terminated poly (ethylene glycol), (PEG). At the same time the attachment of such groups preserves the desirable absorption and emission characteristics. The same technology is also effective for a wide variety of other near infrared dyes. See, U.S. Pat. No. 5,403,928.

Further significant advances have been made in the ability to measure the relevant parameters in immunoassays. For example, using the technique described in Dandliker et al, U.S. Pat. No. 5,302,349, entitled "Transient State Luminescence Assay Apparatus" incorporated here by reference, in its entirety, including any drawings, allows the concentrations of the bound and free forms of the components to be determined in a homogeneous assay format, i.e. no separation of bound and free is required.

Despite the significant and promising improvements made in the field of fluorescent labels and in the data analysis aspect there remains a need in the art for additional dyes which have the essential advantages but are also easier to prepare and have greater chemical stability. Prior closely related art by others is to be found in U.S. Pat. Nos. 5,135,717, 5,346,670, and 5,494,793.

THE INVENTION

The invention can be specified and described as the discovery and application of the finding that certain phthalocyanines can be converted into fluorescent dyes that are useful in making fluorescent probes. This can be accomplished by providing the phthlocyanine with an appropriate metal atom carrying axial ligands with only a few atoms, and as a necessary addition by ring substitution to provide ionic electrical charge, usually negative. These changes largely eliminate molecular stacking (face to face aggregation) and also nonspecific binding to other molecular surfaces carrying electrical charge of the same sign.

BRIEF DESCRIPTION OF THE INVENTION

The present invention stems from an unexpected result that even very small groups, such as —OH, can produce effective protection against nonspecific binding and stacking of a planar molecule if two such groups are present one on either side of the molecular plane, and if the net charge of the entire molecule is sufficiently large.

Thus, one aspect of this invention is that the desirable effects of engineering phthalocyanines and other fluorescent dyes by coupling to polyoxyhydrocarbyl groups can be accomplished instead by two very small axial ligands (such as —OH) provided that the net charge on the dye is sufficiently large. For most circumstances this net charge preferably is negative, since in the physiological pH range most biological materials including proteins and DNA will also carry a negative net charge. Thus, we have found that certain sulfonated dihydroxysilicondicarboxyphthalocyanines, particularly La Jolla Blue-3 (LJB-3) when used to label antibody provides a conjugate of high activity and specificity. LJB-3 is much more easily prepared than dyes/fluorophores which carry axial polyethylene glycol (PEG) and in addition, LJB-3 is much more stable chemically. FIG. 1 shows the presumed structure of (LJB-3). The position of the sulfo group is uncertain and could conceivably be on any one of the otherwise unsubstituted benzo rings. The near infrared absorbance maximum for LJB-3 is at 679 nm.

The performance of a fluorophore (fluorescent moiety) can be partly assessed by measurements on the free dye i.e., not in a complete fluorescent probe. Meaningful parameters in this kind of test include fluorescence intensity and polarization/anisotropy which usually are altered when the fluorophore is exposed to different ionic strengths, specific ions or biomolecules such as are present in blood serum. These effects may be thought of as "solvent effects" and may be produced either by changes in the interactions between molecules of the fluorophore to change the state of aggregation or between fluorophore molecules and the components of the solvent (nonspecific binding, NSB).

The contrast between the dye structure of the present invention and those structures of previous attempts to use phthalocyanines (Pc's) as labels for fluorescence probes can be appreciated by a test format for NSB in which the free dye is added to serum and the resulting polarization or anisotropy is measured. An increase in polarization results if nonspecific binding occurs because the increase in molecular mass upon binding results in a decrease in the rate of rotary Brownian motion.

In Table 1 the performance of any one dye can be judged by the changes in fluorescence intensity (I), and/or the changes in polarization (mp, milli-polarization units) as one proceeds horizontally across the table. The "perfect" fluorescence label would have the same values for each of these parameters regardless of the solvent composition.

Comparison of the behavior in normal human serum to that in glycerol is informative since this provides a measure of the loss of potential polarization change by NSB in the presence of serum. For the five dyes listed the values of the differences between the polarization in glycerol and that in normal human serum are: 60.4, 73.6, 103, 12, 61 and 44.1. These differences show a dramatic beneficial effect of Si as a central atom and also point to LJB-3 as the best choice of the group. The ratio of intensities in glycerol divided by that in normal human serum also is indicative. These going down the table are: 1.46, 1.27, 1.51, 2.91, 4.82 and 0.42, again showing a marked superiority of Si over Al and highly acceptable performance of LJB-3.

Additionally, LJB-3 has both carboxyl and sulfonate groups and can be "activated" in a number of ways, i.e., converted to a structure which will react spontaneously to bond covalently at physiological pH's and ambient temperature with groups (usually amino) on the biomolecule to be labeled. We have used two different activating reagents for the labeling of antibody, viz., carbonyl diimidazole and succinimidyltetramethyluronium tetrafluoroborate (STUT). We have found that the latter reagent is preferable both in the ease of handling and in the reproducibility of the results. This could be due to the greater stability of the intermediate, NHS ester of the dye, when STUT is used. Additionally, the best solvent found for the activation with STUT is DMSO. DMF can be used but probably suffers from unavoidable traces of amines.

The most definitive test for suitability of a fluorophore for a given application is to incorporate the dye into a complete probe and to test the probe. The serum tests above on the free dye are useful guides but cannot fully replace tests made on a specific probe.

Tables 2 and 3 show illustrative results using LJB-3 labeled anti-human IgG as a probe for ANA (antinuclear antibodies). The quality of performance can be measured by the FIU (pos/neg) (or FIU[+/−]) value, i.e., the ratio of signal from a positive sample as compared to that from a negative (normal) control. Values of 7 or greater are useful; the data in these tables were obtained as the technology was being developed; in routine use the higher values of FIU(+/−) would be expected to result uniformly.

DETAILED DESCRIPTION OF THE INVENTION

General Discussion

The present invention arises from an unexpected result that even very small groups such as —OH can produce effective protection in aqueous solutions against nonspecific binding and stacking in a planar molecule if two such groups are present, one on either side of the molecular plane and if the net charge is sufficiently large.

Thus, one aspect of this invention is that the desirable effects of engineering phthalocyanine and other fluorescent dyes by coupling to polyoxyhydrocarbyl groups can be accomplished instead by two very small axial ligands (such as —OH) provided that the net charge on the dye is sufficiently large. For most circumstances this net charge preferably is negative, since in the physiological pH range most biological materials including proteins and DNA will also carry a negative net charge. Thus, we have found that certain sulfonated dihydroxysilicondicarboxyphthalocyanines (particularly LJB-3, FIG. 1) have nearly as low non-specific binding to serum proteins as the PEG-conjugated, unsulfonated dye.

In addition, an advantage emerges in that micelle formation by the PEG is absent. The PEG engineered dye at dye concentrations of $10^{-4}$ M and above behaves largely like a macromolecule in that its passage through membranes designed to prevent the passage of molecules of above 30K daltons or more is very impeded. Also, the dye moves in the void volume in gel permeation chromatography designed to separate macromolecules from small molecules. In contrast, LJB-3 behaves as expected for a molecule of its formula weight.

In regard to the non-specific binding as measured by changes in fluorescence polarization and intensity, when the dyes are exposed, for example, to diluted human serum LJB-3 behaves about the same as the PEG coupled dye. In this connection it is important to note that negative charge in itself has a marked influence on decreasing non-specific binding considering that the unsulfonated dihydroxydicarboxysiliconphthalocyanine shows appreciable nonspecific binding. Hydroxyaluminumphthalocyaninetrisulfonate shows both strong sensitivity to ionic strength and also has strong nonspecific binding. It appears that the phthalocyanine molecule must have an axial ligand on both sides of the molecular plane, but that the —OH group is sufficiently large to virtually eliminate nonspecific binding if the net charge is sufficiently high.

Another advantage of the present invention is that dyes engineered by —OH or other small solublizing axial ligands together with high charge appear to be much more reactive chemically (in labeling reactions) even though the molecules being labeled, e.g., proteins and oligonucleotides, are themselves negatively charged. This suggests that the PEG ligands to interfere in labeling macromolecules, although labeling haptens and other small molecules usually proceeds easily.

This invention is very unexpected in a view of the strong nonspecific binding of hydroxyaluminumphthalocyaninetrisulfonate, from which one might presume that dihydroxdicarboxysilicophthalocyanine with a smaller negative net charge would show even stronger nonspecific binding than the aluminum dye. This invention is based in part on findings which show quite the reverse. The effects of other small axial ligands such as: —OCH$_3$, —O—CH$_2$OH, —Cl, —Br and —F also may be useful. The behavior of —OPO$_3$H$_2^-$ is also significant and suggests other potentially useful ligands such as borate and sulfate.

Many other nitrogen containing macrocycles can be metallated with atoms of Group 14 with similar results. Such macrocycles include derivatives and structural variants of porphyrins, azaporphyrins, corroles, sapphyrins, pentaphyrins, porphycenes and other like macrocycles which have extensively delocalized pi electron systems. In view of the fact that they incorporate many desirable characteristics, an especially preferred class of macrocycles comprises azaporphyrin derivatives and structural variants. Azaporphyrin derivatives include derivatives of mono-, di- and triazaporphyrin and prophyrazine. Any of these macrocycles may optionally also have fused aromatic rings. Such azaporphyrin derivatives and variants include phthalocyanine, benzotriazaporphyrin and naphthaloyanine and their derivatives as well as their oxa-, thia-, or aza-structural variants. Certain non-macrocyclic aromatic structures, for example xanthene derivatives may also have the necessary fluorescence properties of the classes enumerated above (Daltrozzo et al., U.S. Pat. No. 6,552,199, Apr. 22, 2003).

The present invention thus relates to marker components, fluorescent probes, natural and synthetic therapeutic drugs, antigens, haptens, antibodies, oligonucleotides, hybridization assays, and immunoassays using such products and methods for making such products. According to the present invention, detectably labeled marker components are provided that comprise a fluorophore moiety coupled to two or more small solubilizing ligands usually axial, the axis being defined by the octahedral geometry of complexes formed by a central metal atom, which preferably reduce or remove the problems of solvent sensitivity and nonspecific binding.

Use of such detectable labels or marker components in assays is advantageous in that these labels have substantially the same intensities of parallel and perpendicular components of fluorescence emission in the presence and absence of biological materials such as serum. Thus, assay methods using these labels are capable of detecting low concentrations of an analyte, a target analyte or analog thereof in biological fluids or on biological surfaces such as tissue samples or cultured cells. The term "analyte" refers to the compound or compound to be measured in an assay which may be any compound for which a receptor naturally exists or can be prepared which is mono or polyepitopic, antigenic or haptenic, a single or plurality of compounds which share at least on common epitopic site or a receptor. The term "target analyte" refers to the compound or compound to be measured in an assay which may be any compound for which a receptor naturally exists or can be prepared which is mono- or polyepitopic, antigenic or haptenic, a single or plurality of compounds which share at least one common epitopic site or a receptor. By "analog" of a target analyte is meant a compound or compounds capable of competing with the target analyte for binding to a receptor. The term "receptor" refers to a molecule complex which is capable of specifically recognizing or being recognized by a target analyte or analog thereof. For example, an antibody may be a receptor for an antigen.

These marker components may be used as labels for labeling an analyte, antigen, antibody or other molecule. These marker components may be optionally functionalized so as to include a linker arm which allows the marker component to be linked to the analyte, antigen, antibody or other molecule. A variety of linker arms which are suited to this purpose have been described. Kricka, J. J.; *Ligand Binder Assays; Labels and Analytical Strategies*; pages 1551; Marcel Dekker, Inc., New York, N.Y. (1985). The marker component is linked to the analyte, antigen, antibody or other molecule using conventional techniques.

In one aspect the present invention provides a detectably labeled marker component which comprises: (1) a fluorescent moiety comprising a luminescent substantially planar molecular structure, preferably having excitation wavelengths of at least about 550 nm and (2) coupled thereto two or more small solubilizing axial ligands and (3) having a sufficiently large negative net charge. Examples of preferred fluorophores, small solubilizing axial ligands, and linkages of the two are described in detail herein. In addition, evidence is provided demonstrating the effectiveness of the axial ligands and the net charge in reducing solvent sensitivity and nonspecific binding.

The term "solvent sensitivity" refers to changes in the fluorescence behavior of a molecule depending on the solvent system in use, most notably referring to differences in fluorescence behavior in aqueous solution in comparison with organic solvents (such as DMF). Many fluorophores which exhibit high fluorescence intensity in organic solvents such as DMF show substantially decreased fluorescence intensity in aqueous solution. Fluorescence intensity is related to sample concentration and the intensity of the exciting radiation. The fluorescence intensity of a particular dye can be correlated to its characteristic light absorptivity (extinction coefficient) and fluorescence quantum efficiency, as well as environmental factors. These marker components also exhibit enhanced decay times which approach their radiative or unquenched lifetimes. We use the term "decay time" generically to indicate the time which must elapse in order for the concentration of excited molecules to decrease from its initial concentration to l/e of that value. Usage of terms regarding lifetime varies, of, for example, Demos, J. N., Excited State Lifetime Measurements, Academic Press, New York, N.Y. (1983), Pages 10, 35, 44, 158.

The performance of a fluorophore can be partly assessed by measurements on the free dye i.e., not in a complete fluorescent probe. Meaningful parameters in this kind of test include fluorescence intensity and polarization/anisotropy which usually are altered when the fluorophore is exposed to different ionic strengths, specific ions or biomolecules such as are present in blood serum. These effects may be thought of as "solvent effects" and may be produced either by changes in the interactions between molecules of the fluorophore to change the state of aggregation or between fluorophore molecules and the components of the solvent (nonspecific binding, NSB).

The contrast between the dye structure of the present invention and those structures of previous attempts to use phthalocyanines (Pc's) as labels for fluorescence probes can be appreciated by the above model for NSB in which the free dye is added to serum and the resulting polarization or anisotropy is measured. An increase in polarization results if nonspecific binding occurs because the increase in molecular mass upon binding results in a decrease in the rate of rotary Brownian motion.

In Table 1 the performance of any one dye can be judged by the changes in fluorescence intensity (I), and/or the changes in polarization (mp, milli-polarization units) as one proceeds horizontally across the table. The "perfect" fluorescence label would have the same values for each of these parameters regardless of the solvent composition.

Comparison of the behavior in normal human serum to that in glycerol is informative since this provides a measure of the loss of potential polarization change by NSB in the presence of serum. For the five dyes listed the values of the differences between the polarization in glycerol and that in normal human serum are: 60.4, 73.6, 103, 12, 61 and 44.1. These differences show a dramatic beneficial effect of Si as a central atom and also point to LJB-3 as the best choice of the group. The ratio of intensities in glycerol divided by that in normal human serum also is indicative. These going down the table are: 1.46, 1.27, 1.51, 2.91, 4.82 and 0.42, again showing a marked superiority of Si over Al and highly acceptable performances of LJB-3 (structure shown in FIG. 1).

Additionally, LJB-3 has both carboxyl and sulfonate groups and can be "activated" in a number of ways, i.e., converted to a structure which will react spontaneously to bond covalently at physiological pH's and ambient temperature with groups (usually amino) on the biomolecule to be labeled. We have used two different activating reagents for the labeling of antibody, viz., carbonyl diimidazole and succinimidyltetramethyluronium tetrafluoroborate (STUT). We have found that the latter reagent is preferable both in the ease of handling and in the reproducibility of the results. This could be due to the greater stability of the intermediate, NHS ester of the dye, when STUT is used. Additionally, the best solvent found for the activation with STUT is DMSO. DMF can be used but probably suffers from unavoidable traces of amines.

Experimental Results

The most definitive test for suitability of a fluorophore for a given application is to incorporate the dye into a complete probe and to test the probe. The serum tests above on the free dye are useful guides but cannot fully replace tests made on a specific probe.

Tables 2 and 3 show illustrative results using LJB-3 labeled anti-human IgG as a probe for ANA (antinuclear antibodies). The quality of performance can be measured by the FIU (pos/neg) (or FIU [+/−]) value, i.e., the ratio of signals from a positive sample as compared to that from a negative (normal) control. Values of 7 or greater are useful; the data in these tables were obtained as the technology was being developed; in routine use the higher values of FIU (+/−) would be expected to result uniformly.

TABLE 2

Specificity of Binding of LJB-3-labeled Goat Anti-Human IgG to patient antinuclear serum antibodies (ANA).

A: Dye preparation: LJB-3[1] activated by carbonyl diimidazole.

| Lot # | n moles LJB-3 | Mole ratio of Dye/protein in product | FIU[2] (+/−) |
|---|---|---|---|
| 211-45-70 J[3] | 70 | 4.1 | 11.7 |
| 211-49-70 D[3] | 70 | 3.4 | 2.4 |
| 211-45-100 J | 100 | 2.0 | 2.1 |
| 211-49-100 D | 100 | 11.8 | 11.9 |
| 211-45-140 J | 140 | 3.1 | 9.2 |
| 211-51 J | 140 | 6.3 | 7.1 |

B: Dye preparation: LJB-3 activated by STUT*

| ID Labeled antibody | Mole Ratio Dye/Protein | FIU Pos/Neg |
|---|---|---|
| 6th Reference | 5.60 | 14.04 |
| 211-184 | 3.44 | 5.86 |
| 211-186 | 1.16 | 5.06 |
| 211-187 | 1.63 | 6.91 |
| 211-190E | 2.09 | 8.87 |
| 6th Reference | 5.60 | 14.30 |

TABLE 1

Changes in Fluorescence Intensity (I) and Polarization (mp) as a Measure of the Sensitivity of Substituted Phthalocyanines to Alterations in Solvent Composition

| Fluorophore | TD$_x$ Buffer | | BBS | | Fetal Bovine Serum | | Normal Human Serum | | Glycerol | |
|---|---|---|---|---|---|---|---|---|---|---|
| | I | mp | I | mp | I | mp | I | mp | I | mp |
| Si Pc monosulfonate | 1762 | −1.5 | 1040 | 0 | 867 | 69.7 | 1133 | 82.6 | 1657 | 143 |
| Si Pc tri/tetrasulfonate | 2337 | −1.0 | 1411 | 3.9 | 1080 | 2.6 | 1420 | 13.1 | 1798 | 86.7 |
| Si dicarboxy Pc monosulfonate (LJB-3)(FIG. 1) | 1230 | −.03 | 741 | 2.0 | 716 | 38.7 | 896 | 95.7 | 1351 | 199 |
| Al Pc trisulfonate | 1108 | 1.7 | 520 | 3.4 | 533 | 60.7 | 1086 | 224 | 3155 | 236 |
| Al Pc tetrasulfonate | 370 | 5.9 | 165 | 5.0 | 170 | 40.3 | 259 | 141 | 1249 | 202 |
| DiphosphatoSidicarboxyphthalocyanine | 1069 | 6.7 | 1078 | 2.4 | 1020 | 64.9 | 1083 | 60.9 | 454 | 105 |

Abbreviations: mp: $10^3$ (polarization); TD$_x$ Buffer: Commercial buffer used in fluorescence polarization assays; Pc: phthalocyanine; BBS: Borate buffered saline (0.25 M NaCl, 0.0232 M boric acid and 0.00179 M sodium tetraborate. The pH is finally adjusted to 8.0+/−0.05 with 1M NaOH). When serum was tested, 25 μl of whole serum was added to 1 ml of BBS (containing 25 μl of the dye already added). Note that the relative concentrations of the various fluorophores is not known so that comparisons of fluorescence intensities are meaningful only when proceeding in a horizontal direction. An alternative to BBS for manipulating LJB-3 in aqueous solutions is borate buffered KCl (BBKCl) which is made by mixing 33.1 ml of 0.70 M boric acid, 4.0 ml of 0.50 M K$_2$B$_4$O$_7$, 75 ml of 4.0 M KCl and water to make 1 liter: pH ca. 8.1.

Fluorescence measurements: These were made in a transient state polarization fluorometer (FAST-1, Hyperion, Inc. Miami, Fla.)

TABLE 2-continued

Specificity of Binding of LJB-3-labeled Goat Anti-Human IgG to patient antinuclear serum antibodies (ANA).

| 211-191 | 0.95 | 13.54 |
|---|---|---|
| 211-192 | 2.65 | 6.48 |

[1] 1 mg of protein (by Comassie Blue) in each labeling.
[2] FIU: Ratio of fluorescence intensities observed in ANA test; A measure of contrast: Sample/Negative control.
[3] Two different antibody preparations: D and J.
*Succinimidyltetramethyluronium tetrafluoroborate Detailed Background and Scope These marker components are useful as fluorescent labels for incorporation in fluorescent probes. The term "fluorescent probe" refers to a marker component comprising a fluorophore moiety which is bonded to or coordinates either directly or via a linker arm to an analyte, antigen, hapten, antibody or other molecule which is used in an assay, such as a fluoroimmunoassay to determine the presence of and/or quantify a substance of interest. Some of these marker components are useful as phosphorescent labels. The components of the present invention are also useful as labels for agents for in vivo imaging and also as labels for agents used in in vivo tumor therapy.

Since these marker components are particularly useful in assays using samples of biological fluids, preferred for those uses are fluorophores having excitation and/or emission wavelengths in the near infrared region where interference from the ambient fluorescence of other sample components is minimized. Some samples, such as serum, may exhibit considerable interfering background fluorescent from flavins, flavoproteiris, NADH, etc., when excitation wavelengths less than 500 nm are used.

For certain applications, such as fluorescence polarization immunoassays, preferred fluorophores may also exhibit a high degree of fluorescence polarization when in the bound form, preferably greater than about 10% of the theoretical maximum value for an observable polarization. The term "bound" refers to the condition in which a binding interaction has been formed between a molecule and its specific binding partner. For certain applications such as fluorescence transient state assays, preferred fluorophores are also characterized by measured fluorescence decay times in the range of about 1 nanosecond to about 50 nanoseconds, preferably in the range of about 5 to about 20 nanoseconds. For other applications, such as phosphorescent labels, fluorophores having even longer decay times may be used.

Preferred small solubilizing axial ligands include —OH, —O-t-butyl (possibly useful in the presence of organic solvents), —OCH$_2$OH, —OCH$_2$CH$_2$OH, OCH$_2$CHOHCH$_2$OH, —OCH$_2$CH$_2$—OCH$_2$CH$_2$OH, —OCH$_2$CH$_2$—CH$_2$—O—CH$_2$—CH$_2$CH$_2$OH, —OPO$_3$H$_2$, —OB(OH)$_2$, Cl, Br and F.

In preferred embodiments, the fluorophore moiety has a substantially planar, multidentate macrocyclic ligand coordinated to a central atom capable of coordinating with two small solubilizing axial ligands. For use as marker components in fluorescence binding assays, suitable central atoms are those to which may coordinate two axial ligands and which are not of high enough atomic number to cause extensive fluorescence quenching by transition to the triplet state. Preferred elements for the central atom include silicon, germanium, and tin, especially preferred are silicon and germanium.

Use of such detectable labels or marker components of this invention in immunoassays is advantageous in that these labels have substantially the same intensities of parallel and perpendicular components of fluorescence emission in the presence and absence of biological fluids such as serum. Thus, assay methods using these labels are capable of detecting low concentrations of target analyte in biological fluids.

The methods of the present invention are particularly suitable for use with the improved fluorescence detection system described in commonly assigned U.S. Pat. No. 5,323,008 entitled "Fluorometer Detection System."

In competitive inhibition assay procedures utilizing fluorescence labels the present invention is directed to a method of determining the presence of amount of a target analyte by contacting the sample suspected of containing the target analyte with a known quantity of added target analyte or analog thereof linked to a fluorescent probe which includes a detectably labeled marker component made up of a fluorescent moiety which includes a luminescent substantially planar molecular structure coupled to two small solubilizing axial ligands, one located on either side of the planar molecular structure together with a sufficient negative net charge, contacting the mixture with a receptor capable of specifically recognizing the target structure and determining the amount of fluorescence probe either bound to receptor or free. The amount of analyte in the unknown samples may be deduced from readings of the blank samples and of samples containing known amounts of target analyte.

In another aspect, the present invention provides a method for performing a "sandwich" or "two-site" immunoassay having the steps of: (a) contacting a sample suspected of containing a target analyte with a first receptor capable of specifically recognizing the target analyte to form a complex of the target analyte and the first receptor, the first receptor being labeled with a fluorescent probe which has a fluorophore moiety having a luminescent substantially planar molecular structure coupled to two small solubilizing axial ligands, one located on either side of the planar molecular structure together with a sufficiently high negative net charge; (b) contacting the complex with a second receptor capable of specifically recognizing the target analyte or the first receptor, the second receptor being bound to a solid carrier, to form a complex of the first labeled receptor, the target analyte and the second receptor bound to the solid carrier; and (c) measuring either the amount of labeled first receptor associated with the solid carrier or the amount of unreacted labeled first receptor.

In another embodiment, the assay may incorporate the additional step of relating the amount of labeled first receptor measured in the unknown sample to the amount of labeled first receptor measured in a control sample free of the target analyte, or to the amount of labeled first receptor measured in samples containing known quantities of target analyte.

In another aspect, the present invention provides a sandwich-type fluorescence immunoassay method useful for measurement of a target analyte for which two different receptors capable of being recognized by the analyte independently without mutual interference are available. Each receptor is labeled with a different dye. For example, one receptor is labeled with a first dye having absorption and emission maxima of 680 nm and 690 nm, respectively, and the other receptor is labeled with a second dye having absorption and emission maxima of 695 and 705 nm, respectively. Detection and quantification of the analyte can be made using either steady state or transient state measurements. In either case, for the example given, excitation would be at 680 nm and detection would be at 705 nm. This type of assay is based on energy transfer and has the advantage that it is homogenous.

In preferred embodiments the markers and probes of the present invention are most advantageously utilized in homogenous mix and read assays monitored by means of transient state, polarized fluorescence in the near infrared region of the spectrum. This combination of formats results in very rapid procedures which can easily be performed in large numbers and easily automated to give numerical readouts. Such assays have built-in features which favor precision and accuracy because of the low background interference afforded by both near infrared wavelengths (low adventitious fluorescence) and transient state technology (avoids Rayleigh and Raman scattering).

The present invention is directed to immunoassays on biological fluids, including serum, plasma, whole blood, urine and intact cells, the latter, e.g., as suspensions or deposited onto a solid surface as for fluorescence microscopy. In measurements on whole blood it is usually advantageous to lyse erythrocytes prior to assay by a lysing agent such as stearoyl-lysolecithin, palmitoyl-lysolecithin or myristoyl lysolecithin.

In one embodiment, the target analyte is a drug or a metabolite of a drug. The drug may be a steroid, hormone, antibiotic, immunosuppressant, antiasthmatic, antineoplastic, antiarrhythmic, anticonvulsant, antiarthritic, antidepressant, or cardiac glycoside. Examples of such drugs include digoxin, digitoxin, theophylline, phenobarbital, thyroxine, N-acetulprocainamide, primidone, amikacin, gentamicin, netilmicin, tobramycin, carbamazepine, ethosuximide, valproic acid, disopyramide, lidocaine, procainamide, quinidine, methotrexate, amitriptyline, mortriptyline, imipramine, desipramine, vancomycin, and cyclosporine.

In another embodiment, the target analyte is a peptide biomolecule or a fragment thereof. Such peptide biomolecules include, for example, a peptide hormone such as luteinizing hormone, follicle stimulating hormone, human chorionic gonadotropin, thyroid stimulating hormone, angiotensin I, angiotensin II, prolactin, insulin, a tumor marker such as carcinoembryonic antigen or a virus such as rubella virus.

The methods of the present invention provide ways of measuring target analytes in concentrations of from about $10^{-5}$ M to about $10^{-13}$ M, and particularly in the concentration range of from about $10^{-9}$ M to about $10^{-12}$ M. These measurements are very sensitive to both the amount of adventitious fluorescence in the sample or in the receptor preparation and to the intensity of the fluorescence emission. Generally, it is safe to say, that moving the wavelength into the near infrared and utilizing transient state detection are advantageous but the differences in impurities present in each type of sample require that optimization be done for each type of assay during assay development.

It is a principal object of this invention to provide improved fluorescence based assays with greatly enhanced reliability and convenience. It is yet another object of this invention to provide methods which allow rapid and accurate determination, often within a matter of minutes. It is an object of this invention to provide methods which are capable of measuring extremely low concentrations of fluorescence labels or markers. It is an object of this invention to provide methods useful for the clinical setting in that they are rapid and accurate, of relatively low cost and capable of use with unmodified biological samples, such as whole blood. These objectives are best realized by 1) optimization of the optical characteristics of the fluorescent marker, 2) high sensitivity and stability of the detection system, 3) use of transient state detection which removes Rayleigh and Raman scattering, 4) making the assays homogeneous to eliminate separations and to afford simple mix and read procedures and 5) miniaturizing equipment and sample size.

The present invention also provides a method of synthesizing a marker component by reacting the fluorophore moiety with a reactive form of the solubilizing axial ligands. The invention also features a fluorescent probe having, a marker component of the invention, linked to one member of a specific binding pair or a target analyte of an analog. The term "specific binding pair" refers to two different molecules (or compositions) wherein one of the molecules has an area on the surface or in a cavity which specifically recognizes and binds to a particular spatial and polar organization of the other molecule (or molecular complex involving other molecule).

The fluorescent dyes of this invention have applications to several areas of DNA technology and research. In a general way these applications are those in which a single-stranded DNA sequence must be labeled in order to be able to trace and visualize its activities in a process or test. For example, in the Sanger method for DNA sequencing, a primer molecule (a short sequence of DNA complementary to a short part of the 3' end of the template) is end labeled (on the 5' end of said primer). DNA polymerase with the four nucleotidetriphosphates is then used to extend the 3' end of the primer sequence toward the 5' end of the template, producing a new strand complementary to the template. Before the reaction has progressed very far the reaction mixture is split into four equal parts and each part is treated separately with one of the four (A, T, G or C) dideoxynucleotide triphosphates to randomly stop the chain extension and to thus produce a mixture of new sequences of varying lengths terminating in the same base (A, T, G or C) contained in the dideoxynucleotidetriphosphate used. This mixture of new chains of varying lengths is separated by PAGE electrophoresis which separates according to chain length and which can be visualized by a Southern blot in which the pattern of bands is transferred into a nitrocellulose membrane by "blotting" for observation.

In other instances where Southern blots are used the DNA usually has been denatured by high pH and is hence single-stranded. In any of these situations, hybridization with a complementary probe carrying a fluorescent label of this invention offers a means of high sensitivity and specificity for visualizing the DNA from a Southern blot.

DNA fingerprinting is another area which may be expected to be of increasing importance. In one fingerprinting procedure, test probes (labeled single stand sequences) are hybridized with the single strand material in Southern blots from restriction-enzyme-digested DNA from the sample to be identified. Applied this procedure a fluorescent label offers high sensitivity combined with visual detection.

The unique properties of the fluorescent dyes of the present invention could engender totally new types of assays for minute amounts of DNA. These assays would utilize transient state fluorescence polarization (TSFP) with a numerical readout. The outstanding advantage of such assays is that they can be simple mix and read assays done on a microliter scale with no separation necessary. A prototype assay for detection and identification of DNA could proceed as follows:

1. Collect a sample possibly containing DNA to be detected.
2. Amplify the sample by PCR (polymerase chain reaction).
3. Add a single stranded DNA labeled with a fluorescent dye of this invention to the amplification mixture and follow the TSPF with time (perhaps a few minutes). If DNA complementary to the labeled DNA probe was present in the test sample hybridization will take place and the polarization will increase with time.

The present invention is also directed to novel dye-oligonucleotide conjugates and methods of synthesizing them and of using them. Methods of using these conjugates or probes may involve nucleic acid hybridization, nucleic acid amplification and nucleic acid sequencing methods. The dye portion of the dye-oligonucleotide conjugate is a fluorescent marker of this invention. These markers may have a variety of functional groups attached for coupling to DNA or RNA. These functional groups include carboxyl, amino and N-hydroxysuccinimide ester (NHS ester).

By "oligonucleotide" is meant a relatively short chain of nucleotide residues. Typically, an oligonucleotide useful in the present invention has a length of from 5 to 50 nucleotides. The oligonucleotide probes used in the method of the invention include polynucleotides of DNA, RNA or any other kind of sequence hybridizable to nucleic acid sequences. It will be appreciated that such nucleic acid sequences may include base analogues as well as the naturally occurring bases cytosine, adenine, guanine, thymine and uracil. Such base analogues include hypoxanthine, 2.6-diaminopurine and 8-azguanine. The probes may be in double stranded or single stranded form but are preferably in single stranded form. They may be prepared by direct synthesis, polymerase mediated extension reactions or by cloning or any other convenient method. By "linked" is meant combined chemically by an intermediate molecule which is connected to both moieties.

Linkage of the oligonucleotide or polynucleotide to the marker may be accomplished using condensation reactions leading, for example, to the formation of amide, ester, hydrazone, semicarbazone, thiosemicarbazone, urea, and thiourea bonds. For example, a linker may terminate in an amino group, preferably primary. Other linkers may terminate in a carboxyl group.

In another aspect, the present invention provides methods for preparing certain dye-conjugated oligonucleotides. In one embodiment, such a method involves the steps (a) of reacting an oligonucleotide having an attached linker terminating in an amino group with an N-hydroxy succinimide ester or an imidazolide of a detectably labeled marker component which comprises a fluorophore moiety comprising a luminescent substantially planar molecule structure coupled to two small solubilizing axial ligands, one located on either side of the planar molecular structure and having sufficient additional negative charge to depress both aggregation and nonspecific binding, to form a conjugate; and separating the conjugate formed in step (a) from unreacted oligonucleotide or polynucleotide and from unreacted dye. Attachment of a linker to the oligonucleotide can be accomplished by using a diamine or an amino alcohol. Preferably, the detectably labeled marker component comprises a caged dicarboxy silicon phthalocyanine dye.

Alternatively, preparation of the dye-conjugated oligonucleotides may be accomplished: reacting a marker component with a carbodiimide in the presence of hydroxybenzotriazole and in the presence of an oligonucleotide or polynucleotide to form a conjugate; and separating the resulting conjugate from other components of the reaction mixture.

In another aspect, the present invention is directed to a method for the detection of a target nucleic acid sequence in a sample comprising the steps of contacting sample nucleic acid with an oligonucleotide labeled with a fluorescent marker of this invention said oligonucleotide being capable of hybridizing with said target nucleic acid sequence in homogenous solution, and detecting the presence or amount of such hybridization by transient state (or steady state) polarized fluorescence.

In a further aspect, the present invention is directed to methods for detection or quantification of a target nucleic acid wherein the target nucleic acid is a product of nucleic acid amplification. Nucleic acid amplification methods include polymerase chain reaction (PCR), ligase chain reaction (LCR), self-sustained sequence replication (3SR) and transcript-based amplification systems (TAS).

The methods of the present invention are particularly useful when used with a time-correlated transient state detection system, as described in commonly assigned Studholme, et al., U.S. Pat. No. 5,323,008 entitled "Fluorometer Detection System." That system features transient state detection permitting direct readout of the time-dependent polarization of the sample. The system uses a laser diode which can be modulated at very high frequencies, e.g., MHz rate, and exhibits high output power. Typically the laser "on" time is approximately 2-3 nanoseconds. Photons from the solution are detected using a photomultiplier tube operating in a single photon counting mode. The photon event along with the relative time of the photon event, as compared with the laser pulse time, is determined. By storing the individual photon event times a histogram of frequency of photons as a function of time is generated.

In another aspect, the present invention provides a method for monitoring the kinetics of a nucleic acid amplification process, and/or quantifying nucleic acid in a target sample. For example, during amplification by PCR, a probe consisting of an oligonucleotide which has been both "capped" and labeled with a fluorescent dye of this invention may be added directly to the PCR reaction. By "capped" is meant that the 3' end has been reacted with a dideoxynucleotide-triphosphate. Transient state detection of the time dependence of the fluorescence can then be used to follow the reaction as it progresses.

At each cooling phase, the hybridization with amplified product may be followed kinetically. As the concentration of amplified product increases, the rate of combination of probe with amplified product increases and quantifies the concentration of amplified product. This information together with the number of cycles quantifies the amount of DNA present originally in the sample before amplification.

Another aspect of this invention is the broad scope of application to any design, variation or modification of fluorometers. This breadth of applicability is well illustrated in the following example of a specialized type of instrument. In non-absorbing media a light wave traversing medium A surrounded by a second medium B of lower refractive index undergoes total internal reflection at the boundaries of medium A if the angle of incidence is greater than the critical angle. However, the electromagnetic field of the totally reflected light penetrates the boundaries for a short distance and there can produce physical effects such as the excitation of fluorescent molecules located near the interface between A and B.

This effect enables homogenous, fluorescence-based assays in which the specific reaction occurs with molecules immobilized on the surface of medium A and hence at the interface which is the only location where excitation of fluorescence can occur. A simple glass or plastic plate acts both as an optical waveguide for the incident light and as a carrier for specific receptor previously deposited at known locations on the surface. This methodology has been termed "evanescent light fluoroimmunoassay" (Herron et al. U.S. Pat. No. 5,512,492).

Advantageously, the present invention incorporates the features of very large Strokes' shifts utilizing fluorescent dyes based upon N-containing macrocycles (classes listed below) which commonly have a near UV excitation region with emissions in the near infrared region of the spectrum. Such dyes are applicable to immuno/receptor assays in either steady state or transient state modes. Excitation sources include mercury arcs, nitrogen lasers and nitrogen laser pumped dye lasers. Alternatively, these same dyes can be excited in the near infrared with diode lasers allowing excellent results with pulsed excitation and transient state detection. The choice of source depends upon the position of the absorption band for the particular dye in question, the preferred mode of excitation and detection, whether steady state or transient state and upon space requirements.

The inclusion of these features in the chemistry and instrument design for "evanescent light fluoroimmunoassay" should lead to very low background together with high signal levels and thus favor high assay sensitivity The summary of the invention described above is non-limiting and other features and advantages of the invention will be apparent from the following description of the preferred embodiments, and from the claims.

Absorbance and Polarization Behavior of Preferred Marker Components

These marker components which comprise a central atom (for example, silicon) coupled to two small solubilizing axial ligands may be characterized by measurements of transient state fluorescence. In such measurements the intensity of the two components polarized either parallel or perpendicular to the direction of polarization of the exciting pulse is monitored over a time period equal to about 3 times the decay time of the marker component. Such curves reflect extinction coefficient, quantum yield, decay time and state of polarization and supply sensitive indications on the chemical and physical condition of the marker component. For example, if the excited state is being deactivated or converted to the triplet state the overall intensities are lowered and the decay times shortened. If the rotary brownian motion of the molecule is being altered by an increase in viscosity or by being bound to a large molecule, the ratio of the intensity of the parallel to the perpendicular component is increased.

Some marker components according to the present invention show, within experimental error of about 5%, the same intensities, decay time and polarization in DMF (an organic solvent) as in SAP (saline azide phosphate, an aqueous neutral buffer). To some extent these properties are shared by other marker component preparations. A distinctive and important property of the marker components of the present invention is a sensitivity to (and lack of binding to) the components in serum which is evidenced by a lack of any significant measured effect of serum on the intensities, decay time or relative magnitudes of the polarized components of the fluorescence. This property is crucial for the marker components to be used for applications such as assays using biological materials.

Preparation Of Preferred Marker Components

According to one method of preparing the preferred marker components of the present invention, the appropriate fluorophore moiety having hydroxy or halide groups as axial ligands is reacted with a reactive form of the solubilizing moiety in a ligand exchange reaction according to the general reaction scheme:

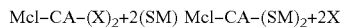

wherein Mcl denotes the macrocyclic ligand, CA the central atom, X the displaced ligand and SM the solubilizing moiety. This reaction may be carried out neat or, if desired, in solvent. Suitable solvents include quinoline, THF, DMF, imidazole (when dissolved in one of the other listed solvents) and the like. Suitable reaction temperatures may vary, depending on the nature of the macrocyclic starting material and the solubilizing group. The reaction is generally complete in about 2 minutes to about 24 hours. The reaction mixture can be conveniently heated under reflux or by means such as a sand bath. For convenience, the reaction may be carried out at ambient pressure. It is believed that this reaction takes place in two steps, with one polyoxyhydrocarbyl group coordinating as an axial ligand at a time.

When used as fluorescent labels in fluorescence immunoassays, these marker components may be linked to one member of a specific binding pair ("labeled binding partner") or an analog of such a member. The term "binding partner" refers to a molecule or molecular complex which is capable or specifically recognizing or being recognized by a particular molecule or molecular complex. The marker component may be directly attached or conjugated thereto or attached or conjugated via a linker arm.

Utility

The marker components of the present invention are useful as fluorescent labels for fluorescent probes and in fluorescence binding assays and also in as labels for in vivo imaging and in vivo tumor therapy.

These marker components may be advantageously used as fluorescent labels in conventional fluorescence binding assays, including fluorescence polarization immunoassays. When so used, these marker components may be linked to one member of a specific binding pair ("labeled binding partner") or an analog of such a member. The marker component may be directly attached or conjugated thereto or attached or conjugated via a linker arm.

These labeled binding partners are useful in assays having a variety of formats, such as assays which involve competition for analyte or analyte binding partner (if a labeled analyte or analyte-analog as used) and may be used in either homogenous or heterogeneous assays.

In view of their advantageous freedom from aggregation in aqueous solution and lack of solvent sensitivity (indicating no detectable aggregation) in combination with their lack of nonspecific binding to serum components and other biological macromolecules, these markers are especially suited for use in assays for detecting an analyte in a sample containing a biological fluid such as serum. Thus, these marker components may be used as labels for fluorescence probes for detecting analytes in solutions where nonspecific binding by serum components would severely compromise sensitivity of an assay, affecting both its accuracy and precision.

Alternatively, these marker components may be used as agents for in vivo imaging. When used as imaging agents, these marker components are conjugated to one member of a specific binding pair to give a labeled binding partner. The labeled binding partner is introduced into an animal. If the other member of the specific binding pair is present, the labeled binding partner will bind thereto and the signal produced by the marker component may be measured and its localization identified.

These marker components may also be used in in vivo tumor therapy. For example, photodynamic therapy involves using the marker component as a photosensitizing agent. The marker component (fluorescent label) is conjugated to a binding partner which may specifically recognize and bind to a component of a tumor cell.

The present invention provides nucleic acid probes and methods of making and using the probes. Methods of using the novel nucleic acid probes include various nucleic acid hybridization sequencing techniques now known or later developed, and various nucleic acid amplification techniques now known or later developed. The probes (also referred to as conjugates herein) and methods of the present invention allow the achievement of 1 fmole sensitivity in a homogenous hybridization assay; this sensitivity is comparable to the sensitivity achieved by current heterogeneous hybridization measurement techniques. As noted above, however, current heterogeneous assays have several disadvantages, which result from the many steps involved in the assays, including increased risk of contamination and increased time required to perform the assays. Other advantages of the compositions and methods of the present invention will be apparent to those in the art upon review of the examples provided herein.

EXAMPLES

To assist in understanding the present invention, the following Examples are included which describe the results of a series of experiments. The following Examples relating to this invention should not, of course, be construed in specifically limiting the invention and such variations of the invention, now know or later developed, which would be within the purview of one skilled in the art are considered to fall within the scope of the invention as described herein and herein after claimed.

Example 1

Synthesis of Tetradiiminopyromellitic Acid Diimide from 1, 2, 4, 5-tetracyanobenzene (TCNB)

TCNB, 20.0 g (0.112 moles) in a 3-neck, 1l flask was dried in vacuo about 1 hr. The flask was fitted with a slow, high torque, Teflon vane stirrer, an inlet for bubbling in ammonia or adding liquid, and a water cooled condenser. After flushing the entire apparatus with nitrogen, 400 ml of methanol was added, stirring was begun at room temperature and ammonia was bubbled in slowly.

The absorption of ammonia is very efficient and after a few minutes the suspension becomes a clear pale green solution. A few minutes later (with constant addition of ammonia) the solution becomes turbid and the temperature rises slightly. After 40 minutes from the beginning of addition of ammonia the reaction mixture had become difficult to stir and 200 ml more methanol was added while stirring and ammonia addition were continued. At this point ammonia absorption was still very efficient as evidenced by the lack of bubbles emerging from the surface of the suspension. After 100 minutes it was necessary to add an additional 175 ml of methanol to enable stirring. After 125 min large amounts of ammonia began to appear at the exit from the condenser and reaction mixture was put into water bath at 45 deg. C. with continued mixing, heating and ammonia addition for an additional 240 minutes. After cooling, the reaction mixture was stored at +4 deg. C. for 24 hrs. The solid was then filtered by suction on Whatman #42 paper and dried in vacuo. Yield 23.2 g (0.109 moles).

Example 2

Synthesis of Bis-chloro (2;3Dicarboxyphthalocyanino) Silicon (IV)

Diiminoisoindoline (30.0 g; 0.207 moles) and tetradiiminopyromellitic acid diimide (10.5 g; 0.050 moles) were pulverized together and dried in vacuo overnight in a one liter, 3 neck flask. The flask was fitted with a Teflon vane mixer, septum, thermometer and reflux condenser with a silica gel drying tube. The apparatus with the stirred reactants was flushed with dry nitrogen and under nitrogen, 600 ml quinoline was added and mixed for 30 min. under nitrogen flow. A uniform, fluid suspension resulted. Thereafter, over a 5 min. period 60 ml silicon tetrachloride was added slowly through the septum. The solution darkened and without heating stirring was continued for 15 min.

Then, with continuous stirring, an oil bath preheated to 195 deg. C. was raised into position to immerse the flask to a level above its contents. After 5 min. the bath temperature had dropped to 175 deg. C. and after another 15 min. the back stabilized at 185-190 deg. C. where it was maintained for an additional 60 min. The bath was then lowered and the reaction mixture was allowed to cool for about 15 min. Nitrogen flow was then started to remove unreacted silicon tetrachloride which was detected by moist pH paper at the condenser outlet. After about 45 min. of ventilation the bath now at 100 deg. C. was replaced to continue heating slowly to about 130 deg. C. to facilitate removal of silicon tetrachloride which was complete by the above test after an additional period of 70 min. when only quinoline fumes were evident.

The bath was then removed and when the reaction mixture had cooled to ca. 80 deg. C. a mixture of 424 ml water and 424 ml concentrated hydrochloric acid was added with mixing. Heat was evolved and the final mixture was acidic. The reaction products stood at room temperature overnight. The next day an additional 424 ml water and 424 ml concentrated hydrochloric acid was added with mixing, and the mixture was allowed to settle at room temperature overnight.

The reaction mixture was then filtered on a Buchner funnel (24 cm paper), washed with water and air dried in the hood overnight. The moist filter cake was stirred in one liter of acetone and filtered. The washed material was dried in the hood for 2 days. The dried material (50 g) was pulverized in a mortar with acetone and the mixture was stirred, filtered and dried in vacuo leaving 47.9 g of a dark finely divided solid.

Example 3

Hydrolysis of Bis-chloro(2;3-dicarboxy Phthalocyamino)Silicon (IV), (Dicarboxydichloro Dye)

Concentrated sulfuric acid (98 ml) was placed in a 250 ml round bottom flask using a long stem funnel to avoid wetting the neck of the flask. With magnetic stirring 16.3 g of dicarboxydichloro dye was added in small portions through a funnel with a shorter stem. The additions were extended over period of about an hour to allow lumps of dye to disperse before adding more solid. A drying tube was attached to the flask and the mixture was heated in an oil bath and maintained at 50 deg. C. for 24 hr.

The reaction flask was removed from the oil bath and cooled in ice. Water (75 ml) was added cautiously in small portions and without cooling, the mixture was heated with stirring in an oil bath at 80 deg. C. for 20 hr. After cooling, the mixture was poured into ice in a one liter beaker and stirred.

The mixture was centrifuged at room temperature at 2000×g for 30 min. The sediment was suspended in water (ca. 250 ml) and again centrifuged. This washing was repeated once more, the sediment was collected and suspended in 300 ml 1M $K_2CO_3$. The mixture was heated with stirring in a beaker covered with a watch glass. In 10 min. the temperature reached 90 deg. C. and heating was continued at about 93 deg. for 50 min. more. While still hot the mixture was acidified with concentrated HCl and allowed to cool and stand at room temperature for 2 days.

The solid was then collected on a Buchner funnel, 11 cm with Whatman #42 paper, the filtration taking ca. 1 hr. The solid was washed on the funnel with 3×100 ml portions of water and air dried in the hood. The solid was then 15 broken up and dried in vacuo over $P_2O_5$ and KOH. Yield 13.3 g (87%).

Example 4

Purification of Bis-hydroxy (2,3Dicarboxyphthalocyanino) Silicon IV (Dicarboxy Dye) by Adsorption Chromatography on Silica Crude dicarboxy dye, 3.0 g, produced as in Example 3, was placed in a 250 ml bottle to which was added 100 ml MeOH containing 2% (v/v) ethyldiisopropyl amine (DIEA) and the mixture was stirred for 30 min. After this time 43 g silica (EM Science) was added and the mixture was shaken by hand to form a dark paste. After 20 min. an additional 100 ml MeOH with 2% DIEA was added, the bottle was inverted a few times and the contents were stirred for 20 min. Adjustment of the solvent characteristics by adding EtOH in addition to MeOH and DIEA alters the composition of the dye extracted and enables extraction of a single component. The solid was then filtered on a sintered glass funnel (fine porosity, 6.5 cm diameter) under reduced pressure. To prevent too great loss of MeOH the reduced pressure was maintained by connection to a partially evacuated tank. After filtering overnight, the residue was washed with 2×50 ml portions of MeOH+DIEA which required about 30 hr. The filtrate (230 ml) was concentrated in a rotary evaporator to near dryness. The residue was dissolved in 14 ml MeOH+ DIEA and the solution was divided equally and put into two 40 ml conical centrifuge tubes.

The contents of each tube was acidified with 200 ul concentrated HCl and water was added to nearly fill the tubes. The contents were mixed by inverting and shaking few times, and centrifuged at about 650×g for 30 min. The brown supernatant liquid was discarded and the sediment was washed three times with 0.01 M HCl. The sediment was transferred to a 100 ml round bottom flask and the mixture was dried by rotary evaporation and then in vacuo over $H_2SO_4$ and KOH. Wt dry was 304 mg (purified dicarboxy dye).

Example 5

Sulfonation of Purified Dicarboxy Dye by Chlorosulfonic Acid

Purified dicarboxy dye (Example 4), 161 mg, was weighed into a 50 ml long neck, round bottom flask with a magnetic mixer. At room temperature 3.4 ml of $ClSO_3H$ was added under $N_2$. A small air condenser with $N_2$ balloon was attached and the flask and contents was heated in an oil bath at 110 deg. for about 3.7 hr. at which point a µl sample was withdrawn for testing. Heating was then continued for an additional 3.3 hr. at 110 deg. whereupon heating was stopped and a second sample was taken out. Ice was added to both samples and each was diluted with water to a weight of 390 mg. Two ml 1 M $NaHCO_3$ was then added to each sample and the absorbance of each was measured by diluting 10 µl of diluted sample with 2 ml of neutral buffer to make the measurement. For both samples the $A_{max}$ was at 690 nm, the 3.7 hr. sample reading 0.650 and the 7 hr. sample reading 0.490 indicating about 25% destruction of the dye in the last 3.3 hr. heating period. Alternatively, sulfonation can be carried out by heating purified dicarboxy dye in $ClSO_3H$ for 36 hr. at 70 deg. C.

The main reaction mixture was added in small portions to ice in a beaker, and the cold mixture was centrifuged at about 700×g for 30 min. The very faintly colored supernatant liquid was discarded. The sediment was suspended in 30 ml of ice cold water, transferred with water to a 250 nm Erlenmeyer flask, made basic with about 40 ml 1 M $KHCO_3$ and stirred at room temperature overnight. The reaction mixture was transferred to a beaker, acidified with concentrated HCl and stirred at room temperature for 6 hr. and stored at room temperature for 48 hr.

The mixture was centrifuged at ca. 700×g; the colored supernatant fluid was retained and the sediment was dissolved in 1 M $NaHCO_3$ and stirred for 2 hr. The dark greenish solution was passed through a Sep Pak (2 g size, Rainin 25) and the filtrate after acidification was combined with the supernatant fluid from the centrifugation. Total volume was ca. 400 ml. The dark blue acidic solution was adsorbed on a Sep Pak, washed on the column with 3 N HCl and eluted with MeOH. The Sep Pak after washing with MeOH and 3 N HCl can be used over and over. The MeOH eluate containing the dye was dried by rotary evaporation and over $H_2SO_4$ and KOH in vacuo. Yield 158 mg. Purification of this material by chromatography on silica yields La Jolla Blue-3 (LJB-3).

The results are shown in Tables 1 and 2 and characterize the nonspecific binding and solvent sensitivity of the three dyes as assessed by fluorescence intensity and polarization measurements. With regard to intensity, the properties desired are a constancy independent of solvent constituents together with a high fluorescence output. On the other hand, the polarization ideally should remain low in media of low viscosity and be as high as possible in a viscous solvent, such as glycerol.

Table 1 shows that the fluorescence intensity from aluminumphthalocyaninetrisulfonate is very solvent-sensitive. In comparison, dihydroxy dicarboxy silicon phthalocyanine sulfonate shows a dramatically improved performance having almost the same fluorescence output in buffer, buffer plus serum or glycerol alone. Some of this improvement can be seen to be due to sulfonation by comparison with dihydroxy-dicarboxy-silicon-phthalocyanine (no sulfonate groups) which itself is less sensitive to serum and solvent than is the Al compound.

Table 2 indicates even more strongly that the mere presence of the central Si atom results in a lowering of the sensitivity to the environment when compared to Al as a central atom. This difference is most likely due to the fact that Si has two axial ligands and can hence "protect" the planar structure of the dye from solvent effects since a "protecting group" is then present on each side of the molecular plane. In the case of Al only one axial ligand is present and hence one side of the molecular plane is freely accessible to solvent effects. In FIG. 2 the result of this interaction is clearly seen in the very large increase in polarization of the Al dye nearly to the maximum attainable by putting the dye into glycerol (which indicates the approximate limit for the polarization if rotational motion is nearly stopped.)

CONCLUSION

The above exemplary applications relating to the present invention should not be construed as limiting the scope of the invention. Such variations of the invention, now known or later developed, which would fall within the purview of those skilled in the art are to be considered as falling within the scope of the invention as hereinafter claimed.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We Claim:

1. A macrocyclic fluorescent ligand with a central metal atom, said atom having two non-polymeric axial ligands, one on either side of the macrocycle, said axial ligands being chosen from the group consisting of alkoxy, halide, hydroxy, borate, sulfate or phosphate, said macrocycle having one or more benzo groups and as ring substituents on one benzo ring, two ortho carboxy groups or one carboxy group together with one other non-carboxy group having a negative charge at pH 5 or greater in aqueous solutions, and as other ring substituents at any other possible position on the macrocycle one or more non-carboxy groups having a negative charge at pH 5 or greater in aqueous solution, said macrocyclic fluorescent ligand capable of labeling compounds having less red absorbance compared to blue absorbance such that when conjugation of said macrocyclic fluorescent ligand is complete the ratio of the absorbance at 681 nm/350 nm (A red/A blue) is less than 1.5.

2. A macrocyclic fluorescent ligand according to claim 1 in which the macrocycle is a phthalocyanine, the central metal atom is Si or Ge, the axial ligands are hydroxyl and the ring substituents are two ortho carboxy groups on one ring and one sulfo group on one of the other rings.

3. The macrocyclic fluorescent ligand according to claim 1, wherein said macrocycle being a monoazaporphyrin with one or more benzo groups carrying substituents to enable coupling and control of net charge.

4. The macrocyclic fluorescent ligand according to claim 1, wherein said macrocycle being a corrin, sapphyrin, porphycene or naphthalocyanine derivative with substituents to enable coupling and control of net charge.

5. The macrocyclic fluorescent ligand according to claim 1, wherein said macrocycle being a 20-phenyl(5,10,15) tetrabenzotriazaporphyrin or a 20-p-methylphenyl(5,10,15) tetrabenzotriazaporphyrin derivative with substituents to enable coupling and control of net charge.

6. An assay method for quantifying a target analyte in a sample, comprising the steps of: a) contacting the sample with the fluorescent ligand of claim 1, wherein said fluorescent ligand is further comprised of a ligand which binds to a target analyte;

b) allowing the fluorescent ligand to bind to the target analyte;

c) irradiating the sample with electromagnetic radiation having a wavelength that is in the excitation wavelength of the fluorescent ligand;

d) detecting the amount of electromagnetic radiation emitted from the sample that is in the emission wavelength of the fluorescent ligand; and e) quantifying the presence or quantity of the analyte in the sample.

7. A method for detecting a target sequence in a polynucleotide, wherein the method comprises: (a) combining a composition according to claim 1 with a sample containing a oligonucleotide, wherein the oligonucleotide portion of the composition comprises a sequence which hybridizes to the target sequence, to form a hybridization mixture; (b) incubating the hybridization mixture under conditions which yield specific hybridization; and (c) thereafter measuring fluorescence of the hybridization mixture, wherein fluorescence is indicative of the presence of the target sequence.

* * * * *